United States Patent [19]

Greenway

[11] 4,435,414
[45] Mar. 6, 1984

[54] INJECTABLE PENICILLIN COMPOSITION

[75] Inventor: Michael J. Greenway, Worthing, England

[73] Assignee: Beecham Group Limited, England

[21] Appl. No.: 410,328

[22] Filed: Aug. 23, 1982

Related U.S. Application Data

[63] Continuation of Ser. No. 210,603, Nov. 26, 1980.

[30] Foreign Application Priority Data

Nov. 27, 1979 [GB] United Kingdom ................ 7940833

[51] Int. Cl.³ ...................... A61K 31/43; A61K 31/74
[52] U.S. Cl. ...................................... 424/271; 424/78
[58] Field of Search ................................... 424/271, 78

[56] References Cited

U.S. PATENT DOCUMENTS

| 2,715,090 | 8/1955 | Penau et al. | 424/271 |
| 3,141,822 | 7/1964 | Goldberg et al. | 424/271 |
| 3,239,507 | 3/1960 | Naylor et al. | 424/271 |
| 3,549,746 | 12/1970 | Granatek et al. | 424/271 |

OTHER PUBLICATIONS

Lachman et al., *The Theory and Practice of Industrial Pharmacy*, 2nd Ed., Lea & Febiger, Philadelphia, 544-545, (1976).

*Primary Examiner*—Delbert R. Phillips
*Assistant Examiner*—F. T. Moezie
*Attorney, Agent, or Firm*—Jacobs & Jacobs

[57] ABSTRACT

A pharmaceutical composition, which on reconstitution with water yields an injectable solution, which comprises:
(a) sodium dicloxacillin, and
(b) polyethylene glycol or propylene glycol.

7 Claims, No Drawings

INJECTABLE PENICILLIN COMPOSITION

CROSS-REFERENCE

This is a continuation of Ser. No. 210,603 filed Nov. 26, 1980 pending.

This invention relates to an injectable penicillin composition.

More specifically this invention relates to an injectable sodium dicloxacillin composition which has improved solubility at higher injection strengths and at lower temperatures.

Accordingly the present invention provides a pharmaceutical composition, which on reconstitution with water yields an injectable solution, which comprises
 (a) sodium dicloxacillin and
 (b) polyethylene glycol or propylene glycol.

The polyethylene glycol used in this invention may be any having an average molecular weight of less than 10,000. (Higher molecular weight glycols have been found to increase the viscosity to an unacceptable level). It has been found that liquid glycols in the molecular weight range 180–600, especially 200–400, are suitable. However solid glycols, for example those having a molecular weight in the range 1000 to 7000, are particularly preferred. A single glycol or any mixture of glycols may be used.

Normally the weight ratio of the dicloxacillin salt (taken as free acid) to the polyethylene or propylene glycol will be 10:1 to 1:5, more suitably 2:1 to 1:3.

The compositions of this invention may be reconstituted with an aqueous solvent, for example water, in conventional manner, the ingredients either being dissolved simultaneously or consecutively.

Normally sufficient composition will be dissolved to provide a solution containing 50 to 200 mg/ml of dicloxacillin (as free acid), more suitably 100 to 150 mg/ml.

One particularly useful aspect of the invention is an injectable solution containing 125 to 200 mg/ml of sodium dicloxacillin (as free acid), and polyethylene glycol or propylene glycol.

Preferably such solutions contain 125 or 150 mg/ml active ingredient.

The compositions of this invention will normally be presented in glass vials. With a solid polyethylene glycol it will be appreciated that a single vial can contain both the penicillin and the glycol. However with liquid glycols twin packs are generally necessary.

Alternatively the sodium dicloxacillin can be presented in one part of a twin pack or the like, and an aqueous solution of the polyethylene glycol or propylene glycol presented in the other part. Such an arrangement enables the compositions to be reconstituted merely by mixing toether the constituent parts of the pack.

The following Examples illustrate the invention.

EXAMPLE 1

The following Compositions were prepared by mixing together the stated ingredients in the stated proportions.

| Composition Number | Wt. of sodium dicloxacillin (p.f.a.), mg. | Additive |
|---|---|---|
| 1 | 300 | P.E.G. 200: 0.4 mls |
| 2 | 300 | P.E.G. 400: 0.4 mls |
| 3 | 300 | P.E.G. 600: 0.4 mls |
| 4 | 300 | P.E.G. 1500: 200 mg. |
| 5 | 300 | P.E.G. 1500: 400 mg. |
| 6 | 300 | P.E.G. 4000: 400 mg. |
| 7 | 300 | P.E.G. 6000: 400 mg. |
| 8 | 300 | Propylene glyco: 0.4 mls |

EXAMPLE 2

The Compositions prepared in Example 1 were each dissolved in sufficient water to give 2 mls. of clear solution having a sodium dicloxacillin concentration (as free acid) of 150 mg/ml.

I claim:

1. A pharmaceutical composition, which on reconstitution with water yields an injectable solution, of enhanced solubility at higher injection strengths and lower temperatures, which comprises, in the respective weight ratio range of 10:1 to 1:5,
 (a) sodium dicloxacillin, and
 (b) polyethylene glycol or propylene glycol having a molecular weight in the range of 180–7000.

2. A pharmaceutical composition as claimed in claim 1 wherein the glycol is a liquid with a molecular weight range of 180–600.

3. A pharmaceutical composition as claimed in claim 1 wherein the glycol is a liquid with a molecular weight range of 200–400.

4. A pharmaceutical composition as claimed in claim 1 wherein the glycol is a solid with a molecular weight range of 1000–7000.

5. A pharmaceutical composition as claimed in claim 1 wherein the weight ratio of dicloxacillin salt to polyethylene or propylene glycol is in the range 2:1 to 1:3.

6. A pharmaceutical composition as claimed in claim 1 which on reconstitution with water provides an injectable solution containing 125–200 mg/ml of sodium dicloxacillin.

7. A pharmaceutical composition as claimed in claim 1 which on reconstitution with water provides an injectable solution containing 125–150 mg/ml of sodium dicloxacillin.

* * * * *